US00PP14747P2

(12) United States Plant Patent
Trees

(10) Patent No.: US PP14,747 P2
(45) Date of Patent: May 4, 2004

(54) LANTANA PLANT NAMED 'BALUCLEM'

(50) Latin Name: *Lantana camara*
Varietal Denomination: Baluclem

(75) Inventor: Scott C. Trees, Arroyo Grande, CA (US)

(73) Assignee: Ball FloraPlant, a division of Ball Horticultural Co., West Chicago, IL (US)

( * ) Notice: Subject to any disclaimer, the term of this patent is extended or adjusted under 35 U.S.C. 154(b) by 58 days.

(21) Appl. No.: 10/329,582

(22) Filed: Dec. 26, 2002

(51) Int. Cl.[7] ..... A01H 5/00
(52) U.S. Cl. ..... Plt./227
(58) Field of Search ..... Plt./227

*Primary Examiner*—Kent Bell
(74) *Attorney, Agent, or Firm*—Wood, Phillips, Katz, Clark & Mortimer

(57) ABSTRACT

A new and distinct Lantana plant named 'Baluclem', characterized by its yellow flowers upright mounded habit and dark green foliage.

1 Drawing Sheet

Latin name of genus and species of plant claimed: *Lantana camara.*
Variety denomination: 'Baluclem'.

BACKGROUND OF INVENTION

The present invention comprises a new and distinct Lantana plant, botanically known as *Lantana camara*, and hereinafter referred to by the cultivar name 'Baluclem'.

The new cultivar was developed by the inventor in a controlled breeding program during 2000, at Arroyo Grande, Calif. The objective of the breeding program was the development of Lantana cultivars with a well-branched, compact habit, continuous flowering and dark green foliage.

The new cultivar was the result of the open pollination of the female parent Lantana variety 'Simon Yellow' (not patented), which is commercially available, and which exhibits an upright habit and yellow flowers. The new cultivar was selected in December 2000 as a single flowering plant from within the progeny of the above stated cross and was initially designated '353-4'.

Asexual reproduction of the new cultivar at Arroyo Grande, Calif. and West Chicago, Ill. was carried out by the use of terminal stem cuttings has demonstrated that the the new Lantana reproduces true to type with the characteristics of the new cultivar as herein described are firmly fixed and retained through successive generations of such asexual propagation.

SUMMARY OF INVENTION

It was found that the cultivar of the present invention:

(a) exhibits light yellow flowers, (b) forms dark green foliage, and (c) exhibits an upright mounded growth habit.

The new cultivar of the present invention can be compared to the commercially available Lantana variety, Patriot, 'Honeylove' (U.S. Plant Pat. No. 10,011 'Robpathon'). In side-by-side comparison, plants of the new cultivar differ from plants of 'Honeylove'. It is found that the new cultivar has a more compact habit, longer leaves and slightly smaller flowers of a lighter yellow color.

BRIEF DESCRIPTION OF PHOTOGRAPH

The accompanying photographs show as nearly true as it is reasonably possible to make the same in color illustrations of this type, typical flower and foliage characteristics of the new cultivar with one per pot. The plants were grown for 7 weeks in a greenhouse at West Chicago, Ill.

DETAILED BOTANICAL DESCRIPTION

Figure 1:
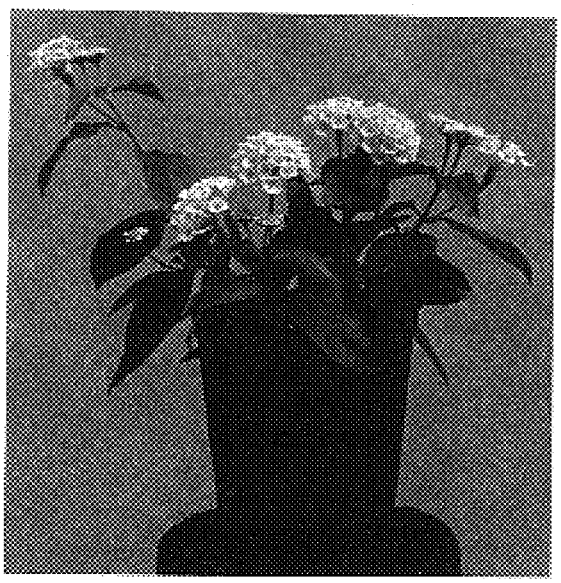
FIG. 1 illustrates the overall growth habit of the new cultivar.
Figure 2:
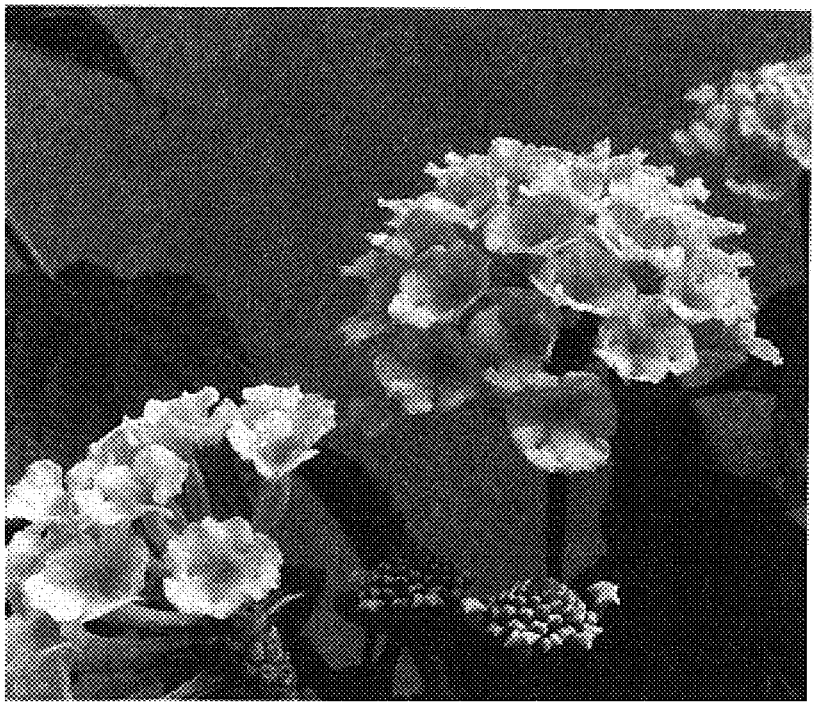
FIG. 2 illustrates a close up view of 4 individual inflorescence of the new cultivar, two of them from a side perspective.

The new cultivar has not been observed under all possible environmental conditions to date. Accordingly, it is possible that the phenotype may vary somewhat with variations in the environment, such as temperature, light intensity, and day length. The chart used in the identification of colors described herein is The R.H.S. Colour Chart of The Royal Horticultural Society, London, England. The color values were determined on Apr. 15, 2002. The readings were taken between 1:00 and 3:00 p.m. under natural daylight conditions. The plants were produced from cuttings taken from stock plants and were grown in a double polycarbonate covered greenhouse under conditions comparable to those used in commercial practice. The plants were grown for 7 weeks while utilizing a soilless growth medium and maintaining temperatures of approximately 75° to 85° F. (24° to 29° C.) during the day and approximately 62° to 68° F. (17° to 20° C.) during the night and light levels of 4,000–10,000 footcandles.

Classification:
*Botanical.*—*Lantana camara* cultivar 'Baluclem'.
Parentage:
*Female parent.*—'Simon Yellow'.
Propagation:
*Type cutting.*—Terminal tip.
*Time to initiate roots.*—Approximately 14 to 21 days.
*Root description.*—Fibrous, branching.

Plant description:

*Habit of growth.*—Moderately vigorous with good branching. Pinching improves branching. A mature plant, 7 weeks after the planting of a rooted cutting, measures approximately 14 cm in height and approximately 23.8 cm in width with 3.4 main branches.

*Form.*—Upright, mounded.

*Branch.*—Square, approximately 10.7 cm in length and 2 mm in diameter, with short soft dense pubescence. Color is 144A. Internode length at middle of stem is approximately 2.4 cm.

*Foliage.*—Leaves are opposite, ovate with serrate/crenate margin, acute apex and attenuate base. Upper surface is densely covered with short, stiff hairs. Lower surface is moderately covered with short stiff hairs while the veins are densely pubescent. Leaf length is approximately 7.1 cm and width is approximately 3.7 cm. Upper surface of mature foliage is 137A and lower surface is 137C. Upper and lower surfaces have pinnate-reticulate venation. Color of venation on upper surface is 144C. Color of venation on lower surface is 145C. Petiole surface is moderately pubescent, length is approximately 8 mm, diameter is approximately 1 mm and color is 145C.

Flowering description:

*Flowering habit.*—Freely flowering.

*Natural flowering season.*—Year round in greenhouse environment and spring through autumn in outdoor garden.

Inflorescence description:

*Shape.*—Spherical.

*Size.*—Approximately 2.7 cm in depth and approximately 4.3 cm in diameter with approximately 42 fully open flowers at any one time. Each flower is subtended by a single bract. Flowers are sessile.

*Bract.*—Shape: Lanceolate. Length: Approximately 1 cm. Width: Approximately 3 mm. Apex: Acute. Margin: Entire. Texture: Both surfaces and the margin are slightly pubescent. Upper surface is 137A; Lower surface is 137B.

*Peduncle.*—Shape: Rectangular. Length: Approximately 5.4 cm. Diameter: Approximately 1 mm. Color: Closest to 144A.

Flower description:

*Fragrance.*—Lemon.

*Lastingness of bloom.*—Approximately 6–9 days.

*Aspect.*—Cupped.

*Bud.*—Square, pillow shaped, approximately 5 mm in width and 3 mm in depth and 11B in color.

*Petals.*—Five, fused at base forming corolla tube. Petals are non-overlapping and non-symmetrical. Upper petal: Shape: Obovate. Apex: Broadly acute. Margin: Entire, undulate. Length from throat: Approximately 5 mm. Width: Approximately 8 mm. Lateral petals: Shape: Obovate. Apex: Obtuse. Margin: Entire, undulate. Length from throat: Approximately 3 mm. Width: Approximately 5 mm. Lower petals: Shape: Obovate. Apex: Obtuse. Margin: Entire, undulate. Length from throat: Approximately 3 mm. Width: Approximately 6 mm.

*Corolla.*—Diameter is approximately 1.2 cm. Petal color when fully open: Upper surface is 10B at margin and center; 23A around tube opening. Lower surface is 8D. Upper and lower surfaces of petals are smooth.

*Corolla tube.*—Length is approximately 1.2 cm, diameter at tube opening is approximately 1.3 mm and diameter at base is approximately 1 mm. Pubescence of outer surface is dense. Color of inner surface is 16C on proximal ½ and 23B on distil ½. Color of outer surface is 22B.

*Calyx.*—Tubular, formed by 5 fused sepals with acute tips. Length: Approximately 3 mm. Diameter: Approximately 1 mm. Color of both upper and lower surface: 150C.

*Reproductive organs.*—There are 4 stamens fused to the corolla tube. The anther length is less than 1 mm and the color is 164C. Pollen is moderate and 1D in color. There is one pistil, 5 mm in length. The stigma length is less than 1 mm and the color is 145B. The style length is approximately 3 mm and the color is 8C. Ovary length is approximately 1 mm and color is 144C.

Seed/fruit production: Seed/fruit production has not been observed.

Disease resistance: Resistance to pathogens has not been observed.

Hardiness zone: 'Baluclem' is hardy in zones nine (9) and above.

I claim:

1. A new and distinct cultivar of *Lantana camera* plant named 'Baluclem' substantially as herein shown and described, which:

(a) exhibits light yellow flowers, (b) forms dark green foliage, and (c) exhibits an upright mounded growth habit.

* * * * *